US011911355B2

(12) United States Patent
Iversen et al.

(10) Patent No.: US 11,911,355 B2
(45) Date of Patent: Feb. 27, 2024

(54) METHODS AND COMPOSITIONS TO INHIBIT TOLERANCE TO OPIOIDS

(71) Applicant: SEN-JAM PHARMACEUTICAL INC., Huntington, NY (US)

(72) Inventors: Jacqueline Iversen, Lloyd Harbor, NY (US); Thomas A. Dahl, Guilford, CT (US)

(73) Assignee: SEN-JAM PHARMACEUTICAL INC., Huntington, NY (US)

( * ) Notice: Subject to any disclaimer, the term of this patent is extended or adjusted under 35 U.S.C. 154(b) by 0 days.

(21) Appl. No.: 17/471,149

(22) Filed: Sep. 9, 2021

(65) Prior Publication Data

US 2022/0096409 A1 Mar. 31, 2022

Related U.S. Application Data

(63) Continuation of application No. 16/133,522, filed on Sep. 17, 2018, now Pat. No. 11,129,803.

(60) Provisional application No. 62/560,051, filed on Sep. 18, 2017.

(51) Int. Cl.
A61K 31/19 (2006.01)
A61K 31/4535 (2006.01)
A61P 25/30 (2006.01)
A61P 25/36 (2006.01)
A61K 31/192 (2006.01)
A61K 31/445 (2006.01)

(52) U.S. Cl.
CPC .......... *A61K 31/192* (2013.01); *A61K 31/445* (2013.01); *A61K 31/4535* (2013.01)

(58) Field of Classification Search
None
See application file for complete search history.

(56) References Cited

U.S. PATENT DOCUMENTS

| 5,516,803 | A | 5/1996 | Raffa | |
|---|---|---|---|---|
| 9,226,918 | B2 | 1/2016 | Peltz et al. | |
| 10,675,261 | B2 * | 6/2020 | Iversen | A61K 31/445 |
| 11,129,803 | B2 * | 9/2021 | Iversen | A61K 31/192 |
| 2006/0281775 | A1 | 12/2006 | Kelly, II et al. | |
| 2007/0072899 | A1 | 3/2007 | Johnson et al. | |
| 2008/0207601 | A1 | 8/2008 | Sabnani | |
| 2010/0143469 | A1 * | 6/2010 | Bosse | A61K 31/167 |
| | | | | 424/472 |
| 2016/0279112 | A1 | 9/2016 | Iversen et al. | |

FOREIGN PATENT DOCUMENTS

| EP | 2813144 | 12/2014 |
|---|---|---|
| JP | 2004/210800 A | 7/2004 |
| JP | 2015044774 A | 3/2019 |
| WO | 2006076019 | 7/2006 |
| WO | 2016105448 A1 | 6/2016 |
| WO | 2016154028 | 9/2016 |

OTHER PUBLICATIONS

PCT Search Report and Written Opinion Application No. PCT/US18/51384 dated Feb. 14, 2019.
"Dangers of Using Opiates with Potentiators"; http://americanaddictioncenters.org/prescription-drugs/potentiators/, retrieved May 17, 2017.
Christine Case-Lo; "Home Remedies to Ease Opiate Withdrawal Symptoms"; Medically Reviewed by Graham Rogers, MD on Aug. 5, 2016; http://www.healthline.com/health/home-remedies-opiate-withdrawal#/call-a-doctor6.
Mary Earhart; "Home Remedies for Opiate Withdrawal Symptoms"; Updated Sep. 17, 2011; Livestrong.com; http://www.livestrong.com/article/245227-home-remedies-for-opiate-withdrawal-symptoms/.
"Medications for opioid withdrawal"; Addiction Blog; Published Nov. 5, 2011; http://prescription-drug.addictionblog.org/medications-for-opiod-withdrawal/.
U.S. Anwari, S. Iqbal; "Antihistamines and potentiation of opioid induced sedation and respiratory depression"; Wiley Online Library; First published Apr. 15, 2003; vol. 58, Issue 5; May 2003; pp. 494-495; http://onlinelibrary.wiley.com/doi/10.1046/j.1365-2044.2003.03154_18.x.
"How to Endure Acute Withdrawal from Opiates (Narcotics)"; wikiHow; http://www.wikihow.com/Endure-Acute-Withdrawal-from-Opiates (Narcotics).
"Using Over-the-Counter Drugs to Aid Drug Detox From Opiates Benzos and Alcohol"; https://www.futuresofpalmbeach.com/holistic-do-they-work/over-the-counter-drugs, retrieved May 17, 2017.
John M. Swegle, Craig Logemann; "Management of Common Opioid-Induced Adverse Effects"; American Family Physician; Oct. 2006. 15; 74(8): 1347-1354; http://www.aafp.org/afp/2006/1015/p1347.html.
Lindsay H. Burns; "Ultra-low-dose opioid antagonists enhance opioid analgesia while reducing tolerance, dependence and addictive properties"; Recent Developments in Pain Research, 2005: 115-136 ISBN; 81-308-0012-8; Editor: Anna Capasso.
Anonymous: Opioid Prescribing Guidelines Opioid Withdrawal Attenuation COCKTAIL11 , • May 1, 2016 (May 1, 2016), XP055799740, Retrieved from the Internet: URL:https:l/www.oregonpainguidance.org/app /content/uploads/2016/05/Opioid-Withdrawal, 1 page.

* cited by examiner

Primary Examiner — Brian Gulledge
(74) Attorney, Agent, or Firm — Morgan, Lewis & Bockius LLP

(57) ABSTRACT

The present invention provides a method of inhibiting tolerance to an opioid by a human subject in need thereof. The method comprises administering an effective amount of a pharmaceutical composition to the subject during opioid therapy. The pharmaceutical composition comprises a) a non-steroidal anti-inflammatory drug (NSAID); and b) a co-agent selected from the group consisting of: fexofenadine, ketotifen, desloratadine, cetirizine, salts thereof and combinations thereof.

7 Claims, No Drawings

METHODS AND COMPOSITIONS TO INHIBIT TOLERANCE TO OPIOIDS

FIELD OF THE INVENTION

The present invention relates to methods, and compositions, for inhibiting the tolerance to opioids upon opioid therapy.

BACKGROUND OF THE INVENTION

Opioids are a class of drugs that include the illegal drug heroin and analgesics available legally by prescription, such as oxycodone (OxyContin®), hydrocodone (Vicodin®), codeine and morphine. Opioids are powerful pain relievers, but their use is hindered by tolerance to the analgesic effects, physical dependence resulting in withdrawal syndrome, and the possibility of addiction.

Tolerance is the need for progressively higher doses of an opioid in order to maintain the same therapeutic effect, e.g., same reduction in pain. Tolerance typically develops upon sustained opioid therapy. While opioid rotation is currently used to minimize tolerance, this approach requires close monitoring due to variable cross-tolerance and side effect profiles among different patients (Fine, P., *J Pain Palliat Care Pharmacother* 18:75-79. (2004)). In its most severe form, opioid tolerance can manifest as opioid-induced hyperalgesia; that is, the opioid no longer reduces pain but instead increases or induces pain (Fine, 2004). Opioid-induced hyperalgesia is extremely difficult to treat.

Due to the potential dire consequences of opioid use, there is an urgent need to minimize the dosage required by patients to maintain a desired pharmacological effect.

SUMMARY OF THE INVENTION

In one embodiment, the present invention includes methods of inhibiting tolerance to an opioid in a human subject in need thereof. The methods comprise administering an effective amount of a pharmaceutical composition to the subject during opioid therapy. The pharmaceutical composition comprises a) a non-steroidal anti-inflammatory drug (NSAID); and b) a co-agent selected from the group consisting of: fexofenadine, ketotifen, desloratadine, cetirizine, salts thereof and combinations thereof.

In one embodiment, the NSAID is aspirin, ibuprofen, naproxen, diclofenac, diflunisal, etodolac, indomethacin, ketoprofen, ketorolac, meloxicam, nabumetone, oxaprozin, piroxicam, salsalate, sulindac, and tolmetin.

In one embodiment, the NSAID is ibuprofen and the co-agent is fexofenadine. In one embodiment, the amount of ibuprofen is about 150 mg to about 900 mg, and the amount of fexofenadine is about 60 mg to about 180 mg. In one embodiment, the ibuprofen and the fexofenadine are combined into one unit dose. In one embodiment, the ibuprofen and the fexofenadine are in the form of a tablet, lozenge or chewing gum.

In one example, the NSAID is ibuprofen and the co-agent is ketotifen. In one embodiment, the amount of ibuprofen is about 1200 mg to about 1600 mg, and the amount of ketotifen is about 0.5 mg to about 4 mg, e.g., a daily dose of about 2400 mg to about 3200 mg ibuprofen and about 2 mg of ketotifen. In one embodiment, the ibuprofen and the ketotifen is combined in one unit dose. In one embodiment, the ibuprofen and the ketotifen is in the form of a tablet, lozenge or chewing gum.

In one embodiment, the present invention is a pharmaceutical composition comprising a) an NSAID, and/or a salt thereof; and b) a co-agent selected from the group consisting of: fexofenadine, ketotifen, desloratadine, cetirizine salts thereof and combinations thereof. In one embodiment, the pharmaceutical composition includes ibuprofen and fexofenadine. In one embodiment, the amount of ibuprofen is about 150 mg to about 900 mg, and the amount of fexofenadine is about 25 mg to about 200 mg. In one embodiment, the NSAID is ibuprofen and the co-agent is ketotifen. In one embodiment, the amount of ibuprofen is about 800 mg to about 1600 mg, and the amount of ketotifen is about 1 mg to about 2 mg.

DETAILED DESCRIPTION OF THE INVENTION

In one embodiment, the present invention is directed to methods of inhibiting the tolerance to opioids in human subjects. The methods include the administration of particular pharmaceutical compositions.

Throughout this specification, quantities are defined by ranges, and by lower and upper boundaries of ranges. Each lower boundary can be combined with each upper boundary to define a range. The lower and upper boundaries should each be taken as a separate element.

Opioids are substances that act by binding to opioid receptors, which receptors are found principally in the central and peripheral nervous system and the gastrointestinal tract. These receptors mediate both the psychoactive and the somatic effects of opioids. Medically opioids are primarily used for pain relief, including anesthesia. Other medical uses include suppression of diarrhea and suppressing cough.

Opioids include opiates, which are alkaloid compounds naturally found in the opium poppy plant (i.e., *Papaver somniferum*). The psychoactive compounds found in the opium plant include opium, heroin, morphine, codeine and thebaine. Examples of synthetic, or semi-synthetic, opioids include hydrocodone (e.g., Vicodin®, Lorcet®, Lortab®, Percocet®, Percodan®); oxycodone (e.g., OxyContin®) fentanyl (e.g., Duragesic®) methadone (Dolophine®); pethidine (e.g., Demerol®) and hydromorphone (e.g., Dilaudie).

Opioid therapy is the treatment of a human subject with opioids, typically a prolonged treatment with opioids, typically to achieve analgesic effects.

In one embodiment, the methods of the present invention comprise the administration of a pharmaceutical composition to a human subject, in need thereof, in an amount which is effective to inhibit the tolerance to opioids by the subject. A human subject in need thereof is a subject who is to receive, or is receiving, opioid therapy. Administration includes administration by a physician or by self-administration.

Tolerance to an opioid drug is defined as the failure of a steady dose of the opioid to sustain the desired pharmacological effect over time. That is, there is a need to increase the opioid dosage to maintain the initial pharmacological effect, e.g., the original analgesic effect of the opioid. Tolerance to opioids can develop in subjects during opioid therapy.

When administered the pharmaceutical composition of the present invention, the tolerance for a given opioid in a subject is inhibited, i.e., tolerance does not develop or tolerance is minimized. That is, the same dose originally given to the subject for a certain therapeutic effect (e.g., analgesic effect) will remain sufficient, or substantially sufficient, throughout the opioid therapy.

The pharmaceutical composition is administered to the human subject, in need thereof, during opioid therapy, alternatively, slightly before opioid therapy. For example, administration is begun at most about 48 hours before the first dose of an opioid or at the time of the first dose of an opioid, and is substantially continued for the duration of the opioid therapy. Alternatively, administration can be begun at any point during opioid therapy.

In the present specification, the term "inhibit" includes "reduce" and/or "prevent" and/or "shorten duration." That is, the methods of the present invention are considered to be effective if they cause one or more of: a reduction/prevention of tolerance to an opioid and/or shortening of the duration of any tolerance to an opioid. For example, tolerance is inhibited if the same amount of an opioid renders the same, or substantially the same, or greater effect (e.g., analgesic effect) during an opioid therapy. That is, the initial prescribed dose of an opioid is not required to be increased to achieve the same therapeutic effect.

Inhibition of tolerance can be assessed by comparing the magnitude and/or duration of tolerance in a subject at two different occasions, that is, i) when administered the pharmaceutical composition during an opioid therapy; and ii) when not administered the pharmaceutical composition during an opioid therapy. An assessment is made as to whether the same pharmaceutical effect is achieved with substantially the same dose of an opioid throughout an opioid therapy at the different occasions. Inhibition of tolerance can also be assessed by comparing the magnitude and/or duration of tolerance in different subjects being treated with the same opioid, some of whom are administered the pharmaceutical composition during a therapy and some whom are not administered the pharmaceutical composition during a therapy. An assessment is made as to whether the same pharmaceutical effect is achieved with substantially the same dose of an opioid throughout an opioid therapy between the different subjects.

Typically, tolerance is inhibited by at least about 10%, at least about 20%, at least about 30%, at least about 40%, at least about 50%, at least about 60%, at least about 70%, at least about 80%, at least about 90%, or about 100%.

The pharmaceutical composition comprises a) at least one non-steroidal anti-inflammatory drug ("NSAID"), and b) a co-agent.

The NSAID of the present invention includes any NSAID and salts thereof. Examples of suitable NSAIDs include, but are not limited to, aspirin (i.e., acetylsalicylic acid); ibuprofen (i.e., isobutylphenylpropanoic acid); naproxen (i.e., 6-methoxy-α-methyl-2-naphthaleneacetic acid); diclofenac (i.e., 2-[(2,6-dichlorophenyl)-amino]benzene acetic acid); diflunisal (i.e., 2',4'-difluoro-4-hydroxybiphenyl-3-carboxylic acid); etodolac (i.e., (RS)-2-(1,8-diethyl-4,9-dihydro-3H-pyrano[3,4-b]indol-1-yl)acetic acid); indomethacin (i.e., 2-{1-[(4-chlorophenyl)-carbonyl]-5-methoxy-2-methyl-1H-indol-yl}acetic acid); ketoprofen (i.e., 3-benzoyl-α-methylbenzeneacetic acid); ketorolac (i.e., 2-amino-2-(hydroxymethyl)-1,3-propanediol); meloxicam (i.e., 4-hydroxy-2-methyl-N-(5-methyl-2-thiazolyl)-2H-1,2-benzothiazine-3-carboxamide-1,1-dioxide); nabumetone (i.e., 4-(6-methoxy-2-naphthyl)-2-butanone); oxaprozin (i.e., 3-(4,5-diphenyl-1,3-oxazol-2-yl)propanoic acid); piroxicam (i.e., 4-hydroxy-2-methyl-N-2-pyridinyl-2H-1,2-benzothiazine-3-carboxamide 1, 1-dioxide); salsalate (i.e., 2-(2-hydroxybenzoyl)-oxybenzoic acid); sulindac (i.e., {(1Z)-5-fluoro-2-methyl-1-[4-(methylsulfinyl)-benzylidene]-1H-indene-3-yl}acetic acid); and tolmetin (i.e., [1-methyl-5-(4-methylbenzoyl)-1H-pyrrol-2-yl]acetic acid).

Suitable co-agents include desloratadine (i.e., 8-chloro-6, 11-dihydro-11-(4-piperidinylidene)-5H-benzo[5,6]cyclohepta[1,2-b]pyridine); fexofenadine (i.e., (±)-4-hydroxy-4-[1 hydroxy-4 [4-hydroxydiphenylmethyl)-1-piperidinyl]-butyl]-α, α-dimethyl benzeneacetic acid); ketotifen; cetirizine; and salts of such co-agents.

The NSAIDs and co-agents include all pharmaceutically acceptable versions of the NSAIDs and co-agents, including, for example, stereoisomers and/or any mixtures thereof, all pharmaceutically acceptable zwitterions and/or any mixtures thereof, all pharmaceutically acceptable polymorphic forms and/or any mixtures thereof, and all pharmaceutically acceptable complexes (including solvates) and/or any mixtures thereof.

Salts include all salts of NSAIDs and of co-agents which are pharmaceutically acceptable (i.e., non-toxic at therapeutically effective doses). And, salts include their racemates, enantiomers, or any mixtures thereof.

Particularly suitable salts of the NSAIDs comprise alkali-metal salts (e.g., sodium and/or potassium salts), alkaline earth metal salts (e.g., magnesium and/or calcium salts), aluminum salts, ammonium salts, salts of suitable organic bases (e.g., salts of alkylamines and/or -methyl-D-glutamine), salts of amino acids (e.g., salts of arginine and/or lysine). The NSAID salts also include all enantiomeric salts formed with pharmaceutically acceptable chiral acids and/or bases and/or any mixtures of enantiomers of such salts (e.g., (+) tartrates, (−) tartrates and/or any mixtures thereof including racemic mixtures). For example, a typical salt of an NSAID is naproxen sodium.

Examples of suitable salts of the co-agents include ketotifen fumarate, fexofenadine hydrochloride and cetirizine hydrochloride.

The actual preferred amounts of a pharmaceutical composition in a specified case will vary according to the particular composition formulated, the mode of application, the particular sites of application, and the subject being treated (e.g., age, gender, size, tolerance to drug, etc.).

Examples of typical daily amounts of NSAIDs to be administered in the methods of the present invention follows. The daily amounts can be administered in one dose, or in multiple doses, typically, two doses.

Naproxen from about 110 mg to about 1500 mg: Examples of other lower boundaries of this range include about 150 mg, about 220 mg, about 275 mg, about 320 mg and about 420 mg. Examples of other upper boundaries of this range include about 580 mg, about 680 mg, about 780 mg, about 880 mg and about 950 mg.

Ibuprofen from about 100 mg to about 3200 mg: Examples of other lower boundaries of this range include about 200 mg, about 400 mg, about 600 mg, about 700 mg, about 950 mg and about 1000 mg. Examples of other upper boundaries of this range include about 1200 mg, about 1500 mg, about 1600 mg, about 2000 mg, about 2500 mg and about 3000 mg.

Aspirin from about 250 mg to about 4000 mg: Examples of other lower boundaries of this range include about 325 mg, about 450 mg, about 550 mg, about 700 mg, about 1000 mg, about 1500 mg, and about 1800 mg. Examples of other upper boundaries of this range include about 2000 mg, about 2500 mg, about 3000 mg, about 3500 mg, and about 3800 mg.

Examples of typical daily amounts of the co-agent to be administered in the methods of the present invention follows. The daily amounts can be administered in one dose, or in multiple doses, typically, two doses.

Fexofenadine from about 2 mg to about 200 mg: Examples of other lower boundaries of this range include about 60 mg, about 70 mg, about 80 mg and about 90 mg. Examples of other upper boundaries of this range include about 100 mg, about 120 mg, about 150 mg and about 180 mg. Ketotifen from about 0.5 mg to about 3 mg, or about 0.5 mg to about 4 mg: Examples of other lower boundaries of this range include about 1 mg, about 1.5 mg and about 1.8 mg, and about 3.5 mg. Examples of other upper boundaries of this range include about 2 mg, about 2.5 mg and about 2.8 mg. Desloratadine from about 2 mg to about 40 mg: Examples of other lower boundaries of this range include about 5 mg, about 6 mg and about 7 mg. Examples of other upper boundaries of this range include about 8 mg, about 9 mg and about 10 mg. Cetirizine from about 2 mg to about 10 mg: Examples of other lower boundaries of this range include about 5 mg, about 6 mg and about 7 mg. Examples of other upper boundaries of this range include about 8 mg, about 9 mg and about 10 mg.

In one embodiment of the invention, a pharmaceutical composition comprises about 800 mg ibuprofen and about 60 mg fexofenadine. The pharmaceutical composition can be administered every twelve hours beginning before the last dose of an opioid is taken, preferably by delayed release administration.

In one embodiment of the invention, a pharmaceutical composition comprises about 1200 mg to about 1600 mg ibuprofen and about 1 mg ketotifen, administered to result in a daily dose of about 2400 mg to about 3200 mg ibuprofen and about 2 mg ketotifen. For example, the pharmaceutical composition can be administered every twelve hours beginning before the last dose of an opioid is taken, preferably by controlled release administration.

The pharmaceutical composition can be administered by methods known in the art. For example, the pharmaceutical composition can be administered systemically. For the purposes of this specification, "systemic administration" means administration to a human by a method that causes the compositions to be absorbed into the bloodstream.

In one embodiment, the pharmaceutical compositions are administered orally by any method known in the art. For example, the compositions can be administered in the form of tablets, including, e.g., orally-dissolvable tablets, chewable tablets; capsules; lozenges; pills (e.g., pastilles, dragees); troches; elixirs; suspensions; syrups; wafers; chewing gum; strips; films (e.g., orally-dissolving thin films); soluble powders; effervescent compositions; and the like.

The NSAID (and/or salt thereof) and the co-agent can be supplied in combination as one unit dose, or can be supplied individually, e.g., supplied in a package with a unit dose of NSAID and a unit dose of the co-agent.

Additionally, the pharmaceutical compositions can be administered enterally or parenterally, e.g., intravenously; intramuscularly; subcutaneously, as injectable solutions or suspensions; intraperitoneally; sublingually; or rectally (e.g., by suppositories). Administration can also be intranasally, in the form of, for example, an intranasal spray; or transdermally, in the form of, for example, a patch.

The pharmaceutical composition compounds of the invention can be formulated per se in pharmaceutical preparations, optionally, with a suitable pharmaceutical carrier (vehicle) or excipient, as understood by practitioners in the art. These preparations can be made according to conventional chemical methods.

In the case of tablets for oral use, carriers commonly used include lactose and corn starch, and lubricating agents such as magnesium stearate are commonly added. For oral administration in capsule form, useful carriers include lactose and corn starch. Further examples of carriers and excipients include milk, sugar, certain types of clay, gelatin, stearic acid or salts thereof, calcium stearate, talc, vegetable fats or oils, gums and glycols.

When aqueous suspensions are used for oral administration, emulsifying and/or suspending agents are commonly added. In addition, sweetening and/or flavoring agents may be added to the oral compositions.

For intramuscular, intraperitoneal, subcutaneous and intravenous use, sterile solutions of the pharmaceutically compositions can be employed, and the pH of the solutions can be suitably adjusted and buffered. For intravenous use, the total concentration of the solute(s) can be controlled in order to render the preparation isotonic.

A preferred embodiment of the invention is an orally dissolving tablet comprising an NSAID and a coagent with or without a taste masking ingredient, diluents, etc. Such tablet can be administered without water onto the tongue leading to immediate dissolution and is absorbed gastrointestinally or buccally. Orally dissolving tablets can be formulated by a number of techniques including compression and lyophilization, as would be known to a skilled artisan.

Another preferred embodiment of the invention is a lozenge or troche comprising an NSAID and a coagent with or without a taste masking ingredient, diluents, etc. Such lozenge/troche can be administered without water, and can slowly dissolve in the mouth, or can be swallowed or chewed. Such lozenges/troches can be formulated by compression, as would be known to a skilled artisan.

The pharmaceutical compositions of the present invention can further comprise one or more pharmaceutically acceptable additional ingredient(s) such as alum, stabilizers, buffers, coloring agents, flavoring agents, and the like. In some embodiments, orally administered pharmaceutical compositions can contain breathe neutralizers, e.g., peppermint or menthol scents.

The pharmaceutical composition may be administered by controlled release. Controlled release administration is a method of drug delivery to achieve a certain level of the drug over a particular period of time. The level typically is measured by plasma concentration. Methods for controlled release of drugs are well known in the art.

The pharmaceutical compositions can be formulated for controlled release. For example, in one embodiment, the composition can be a capsule containing beadlets, wherein some of the beadlets dissolve instantaneously and some of the beadlets dissolve at delayed times due to different types of beadlet coatings. For example, a controlled release composition can be administered twice a day, twelve hours apart.

In one embodiment, the pharmaceutical composition comprises an active ingredient, wherein the active ingredient consists of: a) NSAID, and b) a co-agent selected from the group consisting of: fexofenadine, ketotifen, desloratadine, cetirizine, salts thereof and combinations thereof.

In one embodiment, the pharmaceutical composition consists of: a) NSAID, and/or salt thereof, b) a co-agent selected from the group consisting of: fexofenadine, ketotifen, desloratadine, cetirizine, salts thereof, and combinations thereof; and c) at least one carrier and/or excipient.

In one embodiment, the pharmaceutical composition consists essentially of the active ingredients of: a) NSAID and/or salt thereof, and b) a co-agent selected from the group consisting of: fexofenadine, ketotifen, desloratadine, cetirizine, salts thereof and combinations thereof. That is, any other ingredients that may materially affect the basic and novel characteristics of the active ingredients of the invention are specifically excluded from the composition. Any ingredient which can potentially cause an undesirable effect/ side effect, including, for example, an allergic response, may materially affect the basic and novel characteristics of the active ingredients of the invention.

The following are some examples of components which may materially affect the basic and novel characteristics of the active ingredients of the pharmaceutical compositions and may be excluded from certain embodiments of the present invention: cyclooxygenase-2-selective inhibitors (i.e., COX-2-selective inhibitors) or prodrugs thereof; sedating antihistamines (e.g., phenyltoloxamine (e.g., phenyltoloxamine citrate), doxylamine (e.g., doxylamine succinate)); antiemetic antihistamines (e.g., dimenhydrinate (Dramamine®), clizines (e.g., cyclizine, meclizine), diphenhydramine (Benadryl®), promethazine (Pentazine®, Phenergan®, Promacot®), and hydroxyzine (Vistaril®)); decongestants; flunixin meglumine (i.e., banamine); 5-HT3 receptor antagonists; cough suppressants (e.g., guaifenesin, dextromethorphan); $H_2$ antihistamines; and corticosteroids.

The aforementioned ingredients may materially change the characteristics of the present pharmaceutical composition due to unwanted effects and/or potential allergic responses.

Examples of unwanted potential effects of COX-2-selective inhibitors, or prodrugs thereof, include an increased risk in the incidence of myocardial infarctions. COX-2-selective inhibitors are compounds which selectively inhibit cyclooxygenase-2 over cyclooxygenase-1, and also include pharmaceutically acceptable salts of such compounds, and prodrugs of such compounds. A COX-2 selective inhibitor is any inhibitor for which the ratio of COX-1 $IC_{50}$ to COX-2 $IC_{50}$ is greater than 1. Examples of unwanted potential effects of sedating antihistamines, decongestants, and diphenhydramine include sleepiness, fatigue, dizziness, headache, dry mouth, difficulty urinating or an enlarged prostate and allergic reactions. Examples of unwanted potential effects of flunixin meglumine include ataxia, incoordination, hyperventilation, hysteria and muscle weakness. Examples of unwanted potential effects of 5-HT3 receptor antagonists include constipation, diarrhea, headache, dizziness and arrhythmias. Examples of unwanted potential effects of guaifenesin include diarrhea, dizziness, headache, hives, nausea or vomiting, skin rash and stomach pain. Examples of unwanted potential effects of dextromethorphan include confusion, constipation, dizziness, drowsiness, headache, nausea or vomiting and stomach pain. Examples of unwanted potential effects of $H_2$ antihistamines include abdominal pain, bleeding or crusting sores on lip, dizziness, fainting, fever and chills. Examples of unwanted potential effects of corticosteroids include fluid retention, edema, weight gain, high blood pressure, headache and muscle weakness.

In one embodiment, the pharmaceutical composition is combined with an opioid during opioid therapy (i.e., instead of the opioid being given separately). That is, an NSAID, a co-agent and an opioid are formulated into a single pharmaceutical preparation, optionally, with a suitable pharmaceutical carrier (vehicle) or excipient, as understood by practitioners in the art. These preparations can be made according to conventional chemical methods, as described above.

In one embodiment, the pharmaceutical composition is administered during methadone detoxification therapy. Such therapy can either be done relatively rapidly in less than a month or gradually over as long as six months.

Opioid therapy can last for about two to eight weeks, or indefinitely. During such period, the pharmaceutical composition can be administered on a substantially daily basis. Daily NSAID use has been associated with adverse gastrointestinal effects (e.g., upset stomach, ulcers). However, when the NSAIDs of the present invention are taken in combination with the co-agents, adverse gastrointestinal effects are surprisingly slight or absent. Thus, it has unexpectedly been found that the components of the compositions of the present invention have a synergistic effect when inhibiting the adverse symptoms associated with the withdrawal from opioids.

Thus, while there have been described what are presently believed to be the preferred embodiments of the present invention, other and further embodiments, modifications, and improvements will be known to those skilled in the art, and it is intended to include all such further embodiments, modifications, and improvements as come within the true scope of the claims as set forth below.

The invention claimed is:

1. A method of inhibiting tolerance to an opioid by a human subject in need thereof, comprising:
   administering an effective amount of a pharmaceutical composition to the subject during opioid therapy, wherein the pharmaceutical composition consists of:
   a) a non-steroidal anti-inflammatory drug (NSAID) that is ibuprofen;
   b) a co-agent that is ketotifen or salt thereof; and
   c) a pharmaceutical carrier, a pharmaceutical excipient, a sweetening agent, a flavoring agent, a taste masking ingredient, a diluent, alum, a stabilizer, a buffer, a coloring agent, a breath neutralizer, a proton pump inhibitor, an emulsifying agent, a suspending agent and combinations thereof,
   wherein tolerance to an opioid is inhibited in the human subject.

2. The method of claim 1 wherein the amount of ibuprofen is about 1200 mg to about 1600 mg, and the amount of ketotifen is about 0.5 mg to about 3 mg.

3. The method of claim 1 wherein the daily dose of ibuprofen is about 2400 mg to about 3200 mg, and the daily dose of ketotifen is about 2 mg.

4. The method of claim 1 wherein the pharmaceutical composition is in the form of a tablet, lozenge or chewing gum.

5. A method of inhibiting tolerance to an opioid by a human subject in need thereof, comprising:
   administering to the subject an effective amount of a pharmaceutical composition during an opioid withdrawal period, wherein the pharmaceutical composition consists of:
   a) about 1200 mg to about 1600 mg of ibuprofen,
   b) about 0.5 mg to about 3 mg ketotifen, and
   c) a pharmaceutical carrier, a pharmaceutical excipient, a sweetening agent, a flavoring agent, a taste masking ingredient, a diluent, alum, a stabilizer, a buffer, a coloring agent, a breath neutralizer, a proton pump inhibitor, an emulsifying agent, a suspending agent and combinations thereof,
   wherein tolerance to an opioid is inhibited in the human subject.

6. The method of claim 5 wherein the daily dose of ibuprofen is about 2400 mg to about 3200 mg, and the daily dose of ketotifen is about 2 mg.

7. The method of claim 5 wherein the pharmaceutical composition is in the form of a tablet, lozenge or chewing gum.

\* \* \* \* \*